US012659711B2

(12) United States Patent
Shriner et al.

(10) Patent No.: US 12,659,711 B2
(45) Date of Patent: Jun. 16, 2026

(54) RESPONDING TO AND ASSISTING DURING MEDICAL EMERGENCY EVENT USING DATA FROM EAR-WEARABLE DEVICES

(71) Applicant: Starkey Laboratories, Inc., Eden Prairie, MN (US)

(72) Inventors: Paul Anders Shriner, Hopkins, MN (US); Gregory John Haubrich, Champlin, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 383 days.

(21) Appl. No.: 18/334,333

(22) Filed: Jun. 13, 2023

(65) Prior Publication Data

US 2023/0328500 A1     Oct. 12, 2023

Related U.S. Application Data

(63) Continuation of application No. PCT/US2021/064425, filed on Dec. 20, 2021.
(Continued)

(51) Int. Cl.
*H04W 4/90* (2018.01)
*A61B 5/00* (2006.01)
(Continued)

(52) U.S. Cl.
CPC .............. *H04W 4/90* (2018.02); *A61B 5/002* (2013.01); *A61B 5/6815* (2013.01);
(Continued)

(58) Field of Classification Search
CPC ........ H04M 3/5116; H04W 4/90; G06F 40/40
(Continued)

(56) References Cited

U.S. PATENT DOCUMENTS 8,531,291 B2    9/2013  Tran
8,818,522 B2    8/2014  Mass et al.
(Continued)

FOREIGN PATENT DOCUMENTS

WO        2020124022 A2    6/2020
WO        2021016099 A1    1/2021

OTHER PUBLICATIONS

"Vitals Aware Services", City of Plymouth Minnesota, Retrieved from: https://www.plymouthmn.gov/departments/public-safety/police/programs-services/vitals, Accessed on: Sep. 25, 2020, 2 pp.
(Continued)

*Primary Examiner* — Maria El-Zoobi
(74) *Attorney, Agent, or Firm* — Shumaker & Sieffert, P.A.

(57)     ABSTRACT

A computing system makes a first preliminary determination that a user of an ear-wearable device is experiencing a potential medical event based on first signals generated by first sensors. The computing system may make a second preliminary determination that the user is experiencing the potential medical event based on a user response captured by the ear-wearable device. The computing system may further determine that the user is experiencing the potential medical event based on both the first preliminary determination and the second preliminary determination. In response to determining that the user is experiencing the potential medical event, the computing system may cause the ear-wearable device to send a wireless communication request to a plurality of companion devices. Furthermore, in response to the wireless communication request being accepted by a companion device, the computing system may send user data via a communication link.

21 Claims, 4 Drawing Sheets

Related U.S. Application Data

(60) Provisional application No. 63/132,646, filed on Dec. 31, 2020.

(51) Int. Cl.
   G16H 40/67 (2018.01)
   G16H 50/30 (2018.01)

(52) U.S. Cl.
   CPC ........... A61B 5/7405 (2013.01); G16H 40/67 (2018.01); G16H 50/30 (2018.01)

(58) Field of Classification Search
   USPC ...................................................... 455/404.1
   See application file for complete search history.

(56) References Cited

U.S. PATENT DOCUMENTS

| | | | | |
|---|---|---|---|---|
| 9,224,180 | B2 | 12/2015 | Macoviak et al. | |
| 9,597,016 | B2 * | 3/2017 | Stone ..................... | A61B 5/112 |
| 10,198,927 | B2 | 2/2019 | Devdas et al. | |
| 10,743,095 | B1 * | 8/2020 | Bergeron .............. | H04W 4/029 |
| 2010/0315225 | A1 | 12/2010 | Teague et al. | |
| 2013/0344806 | A1 * | 12/2013 | Pai ............................ | A61J 1/00 455/41.1 |
| 2014/0266787 | A1 | 9/2014 | Tran | |
| 2018/0353086 | A1 | 12/2018 | Turner et al. | |
| 2019/0268707 | A1 * | 8/2019 | Solum ..................... | G06F 3/017 |
| 2020/0196914 | A1 | 6/2020 | Sacha | |
| 2022/0261468 | A1 * | 8/2022 | Lin ....................... | A61B 5/0295 |
| 2022/0313089 | A1 * | 10/2022 | Burwinkel ........... | H04R 29/008 |

OTHER PUBLICATIONS

International Preliminary Report on Patentability from International Application No. PCT/US2021/064425 dated Jul. 4, 2023, 9 pp.
International Search Report and Written Opinion of International Application No. PCT/US2021/064425, dated Mar. 23, 2022, 12 pp.
Starkey Hearing, "How to Use Find My Hearing Aids to Find Your Missing Hearing Aids", Youtube, Retrieved from: https://www.youtube.com/watch?v=CIJM-1ez7mA, Oct. 12, 2020, 3 pp.
Stewart, "Authentication 101", F5 Tech Brief, 2010, 9 pp., (Applicant points out, in accordance with MPEP 609.04 (a), that the year of publication, 2010, is sufficiently earlier than the effective U.S. filing date, so that the particular month of publication is not an issue.).

* cited by examiner

RESPONDING TO AND ASSISTING DURING MEDICAL EMERGENCY EVENT USING DATA FROM EAR-WEARABLE DEVICES

This application is a continuation of International Application No. PCT/US2021/064425, filed Dec. 20, 2021, which claims the benefit of U.S. Provisional Patent Application 63/132,646, filed Dec. 31, 2020, the entire content of both of which are incorporated herein by reference.

TECHNICAL FIELD

This disclosure relates to ear-wearable devices.

BACKGROUND

Ear-wearable devices are devices designed to be worn on, in, or near one or more of a user's ears. Common types of ear-wearable devices include hearing instruments (e.g., "hearing aids" and "hearing assistance devices"), earbuds, headphones, hearables, cochlear implants, and so on. In some examples, an ear-wearable device may be implanted or osseointegrated into a user. Some ear-wearable devices include additional features beyond just environmental sound-amplification. For example, some modern ear-wearable devices include advanced audio processing for improved device functionality, and controlling the devices, and beamforming, and some can even communicate wirelessly with external devices, including other hearing aids (e.g., for streaming media).

SUMMARY

Among other techniques, this disclosure describes techniques for providing effective broadcasting of an emergency medical event using data from one or more ear-wearable devices. As described herein, an ear-wearable device may determine, based on signals from one or more sensors of the ear-wearable device and/or a user response captured by the ear-wearable device, whether a user of the ear-wearable device is experiencing a potential medical event. The use of the signals from one or more sensors of the ear-wearable device and user response captured by the ear-wearable device to determine whether the user has fallen may reduce over- and under-reporting of medical emergency events.

In one example, this disclosure describes a method comprising: obtaining, by a processing system, first signals that are generated by one or more first sensors that are included in an ear-wearable device; making a first preliminary determination, by the processing system, that a user of the ear-wearable device is experiencing a potential medical event based on the first signals; making a second preliminary determination, by the processing system, that the user of the ear-wearable device is experiencing the potential medical event based on a user response captured by the ear-wearable device; determining, by the processing system, that the user of the ear-wearable device is experiencing the potential medical event based on both the first preliminary determination and the second preliminary determination; in response to determining that the user of the ear-wearable device is experiencing the potential medical event, sending, from the ear-wearable device to a plurality of companion devices, a wireless communication request; and in response to the wireless communication request being accepted by a companion device of the plurality of companion devices, sending user data via a communication link between the companion device and the ear-wearable device, wherein the user data comprises information generated based on second signals generated by one or more second sensors that are included in the ear-wearable device.

In another example, this disclosure describes a computing system comprising: a data storage system configured to store user data related to a user of an ear-wearable device; and one or more processers implemented in circuitry, the one or more processors configured to: obtain first signals that are generated by one or more first sensors that are included in an ear-wearable device; make a first preliminary determination that a user of the ear-wearable device is experiencing a potential medical event based on the first signals; make a second preliminary determination that the user of the ear-wearable device is experiencing the potential medical event based on a user response captured by the ear-wearable device; determine that the user of the ear-wearable device is experiencing the potential medical event based on both the first preliminary determination and the second preliminary determination; in response to determining that the user of the ear-wearable device is experiencing the potential medical event, sending, from the ear-wearable device to a plurality of companion devices, a wireless communication request; and in response to the wireless communication request being accepted by a companion device of the plurality of companion devices, send the user data via a communication link between the companion device and the ear-wearable device, wherein the user data comprises information generated based on second signals generated by one or more second sensors that are included in the ear-wearable device.

In another example, this disclosure describes an ear-wearable device comprising one or more processors configured to: obtain first signals that are generated by one or more first sensors that are included in an ear-wearable device; make a first preliminary determination that a user of the ear-wearable device is experiencing a potential medical event based on the first signals; make a second preliminary determination that the user of the ear-wearable device is experiencing the potential medical event based on a user response captured by the ear-wearable device; determine that the user of the ear-wearable device is experiencing the potential medical event based on both the first preliminary determination and the second preliminary determination; in response to determining that the user of the ear-wearable device is experiencing the potential medical event, send, from the ear-wearable device to a plurality of companion devices, a wireless communication request; and in response to the wireless communication request being accepted by a companion device of the plurality of companion devices, send user data via a communication link between the companion device and the ear-wearable device, wherein the user data comprises information generated based on second signals generated by one or more second sensors that are included in the ear-wearable device.

In other examples, this disclosure describes a computer-readable data storage medium having instructions stored thereon that, when executed, cause one or more processing circuits to: obtain first signals that are generated by one or more first sensors that are included in an ear-wearable device; make a first preliminary determination that a user of the ear-wearable device is experiencing a potential medical event based on the first signals; make a second preliminary determination that the user of the ear-wearable device is experiencing the potential medical event based on a user response captured by the ear-wearable device; determine that the user of the ear-wearable device is experiencing the potential medical event based on both the first preliminary determination and the second preliminary determination; in response to determining that the user of the ear-wearable device is experiencing the potential medical event, send, from the ear-wearable device to a plurality of companion devices, a wireless communication request; and in response to the wireless communication request being accepted by a companion device of the plurality of companion devices, send user data via a communication link between the companion device and the ear-wearable device, wherein the user data comprises information generated based on second signals generated by one or more second sensors that are included in the ear-wearable device.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
FIG. 1 illustrates an example system for responding to and assisting during medical emergency events using data from one or more ear-wearable devices, in accordance with one or more aspects of the present disclosure.
Figure 1:
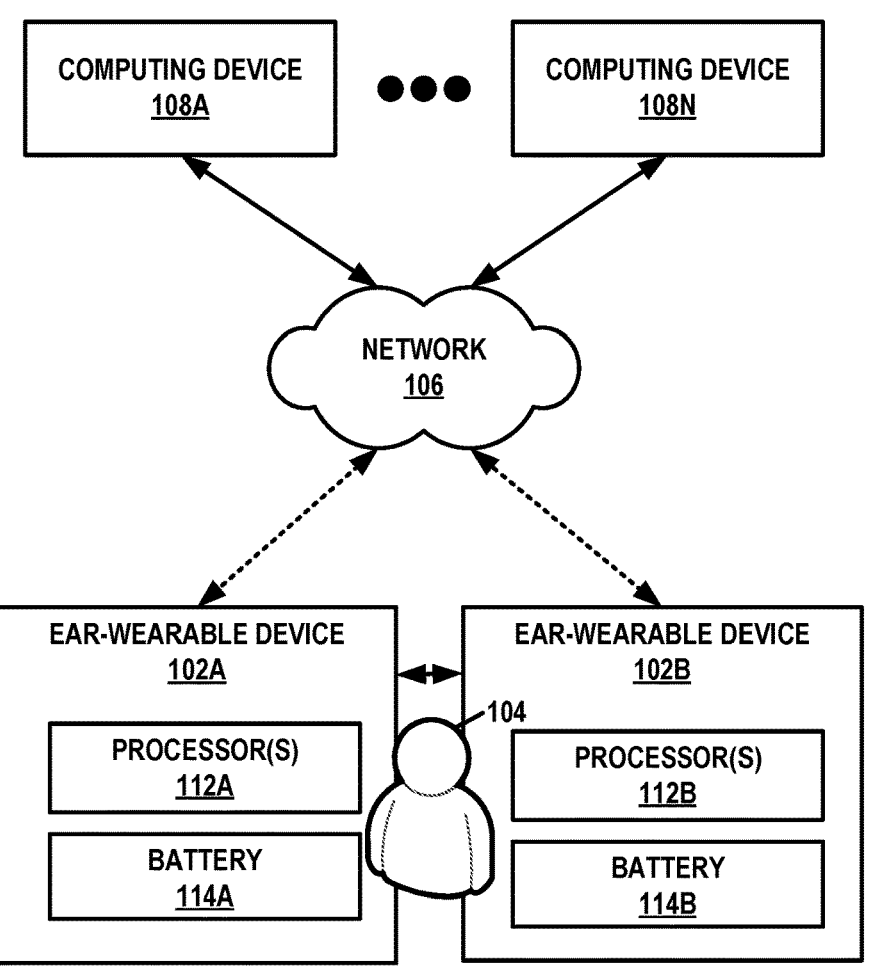

An ear-wearable device may include one or more sensors that gather data about a user of the ear-wearable device. For example, the ear-wearable device may include a heart rate sensor, a photoplethysmography sensor, an inertial measurement unit (IMU), a temperature sensor, a pressure sensor, magnetic field sensors, and so on. The data gathered by such sensors may be used to perform health monitoring activities that track various aspects of the health of the user. For example, the data gathered by such sensors may be used by a health monitoring service in health monitoring activities, such as determining whether the user is experiencing a potential medical event. This disclosure describes techniques for responding to and assisting during medical emergency events using data from ear-wearable devices. For example, a user of an ear-wearable device may experience a medical emergency event (e.g., a stroke, a heart attack, or an Alzheimer's episode) and may be unable to communicate with nearby individuals. Automatically detecting, responding, and assisting during medical emergency events using data from the ear-wearable device may help the user of the ear-wearable device to notify others about the medical emergency event and communicate to others of medical conditions that may be important to determining treatment of the medical emergency event.

As described in this disclosure, a health monitoring system may be implemented that uses data from ear-wearable devices to respond to and assist during medical emergency events. For instance, the health monitoring system may obtain first signals that are generated by one or more first sensors that are included in an ear-wearable device and make a first preliminary determination that a user of the ear-wearable device is experiencing a potential medical event based on the first signals. The health monitoring system may make a second preliminary determination that the user of the ear-wearable device is experiencing a potential medical event based on a user response captured by the ear-wearable device. The health monitoring system may further determine that the user of the ear-wearable device is experiencing a potential medical event based on both the first preliminary determination and the second preliminary determination. In response to determining that the user of the ear-wearable device is experiencing a potential medical event, the health monitoring system may cause the ear-wearable device to send a wireless communication request to a plurality of companion devices. In response to the wireless communication request being accepted by a companion device of the plurality of companion devices, the health monitoring system may cause the ear-wearable device to send user data via a communication link between the companion device and the ear-wearable device. The user data may include information generated based on second signals generated by one or more second sensors that are included in the ear-wearable device. As such, the ear-wearable device may automatically respond to and assist during medical emergency events on behalf of the user of the ear-wearable device.

FIG. 1 is a block diagram illustrating an example computing system 100 for responding to and assisting during medical emergency events using data from one or more ear-wearable devices, in accordance with one or more aspects of the present disclosure. In the example of FIG. 1, computing system 100 includes ear-wearable devices 102A and 102B (collectively, "ear-wearable devices 102"), a network 106, and one or more computing devices 108A through 108N (collectively, "computing device(s) 108). A user 104 may wear ear-wearable devices 102. In some instances, such as when user 104 has unilateral hearing loss, user 104 may wear a single ear-wearable device. In other instances, such as when user 104 has bilateral hearing loss, user 104 may wear two ear-wearable devices, with one ear-wearable device for each ear of user 104. However, it should be understood that user 104 may wear a single ear-wearable device even if user 104 has a bilateral hearing loss. It should also be understood that user 104 may wear two ear-wearable devices even if user 104 has a unilateral hearing loss.

Ear-wearable device(s) 102 may comprise one or more of various types of devices configured to provide hearing assistance. For example, ear-wearable device(s) 102 may comprise one or more hearing assistance devices. In another example, ear-wearable device(s) 102 may comprise one or more Personal Sound Amplification Products (PSAPs). In another example, ear-wearable device(s) 102 may comprise one or more cochlear implants, cochlear implant magnets, cochlear implant transducers, and cochlear implant processors. In another example, ear-wearable device(s) 102 may comprise one or more so-called "hearables" that provide various types of functionality. In other examples, ear-wearable device(s) 102 may comprise other types of devices that are wearable in, on, or in the vicinity of the user's ears. In some examples, ear-wearable device(s) 102 may comprise other types of devices that are implanted or otherwise osseointegrated with the user's skull, wherein the ear-wearable device is able to facilitate stimulation of the wearer's ears via the bone conduction pathway. The techniques of this disclosure are not limited to the form of ear-wearable device shown in FIG. 1. Furthermore, in some examples, ear-wearable device(s) 102 include devices that provide auditory feedback to user 104. For instance, ear-wearable device(s) 102 may include so-called "hearables," earbuds, earphones, or other types of devices.

In some examples, one or more of ear-wearable device(s) 102 includes a housing or shell that is designed to be worn in the ear for both aesthetic and functional reasons and encloses the electronic components of the ear-wearable device. Such ear-wearable devices may be referred to as in-the-ear (ITE), in-the-canal (ITC), completely-in-the-canal (CIC), or invisible-in-the-canal (IIC) devices. In some examples, one or more of ear-wearable device(s) 102 may be behind-the-ear (BTE) devices, which include a housing worn behind the ear that contains all of the electronic components of the ear-wearable device, including the receiver (i.e., the speaker). The receiver conducts sound to an earbud inside the ear via an audio tube. In some examples, one or more of ear-wearable device(s) 102 may be receiver-in-canal (RIC) hearing-assistance devices, which include a housing worn behind the ear that contains electronic components and a housing worn in the ear canal that contains the receiver.

Ear-wearable device(s) 102 may implement a variety of features that help user 104 hear better. For example, ear-wearable device(s) 102 may amplify the intensity of incoming sound, amplify the intensity of certain frequencies of the incoming sound, or translate or compress frequencies of the incoming sound. In another example, ear-wearable device(s) 102 may implement a directional processing mode in which ear-wearable device(s) 102 selectively amplify sound originating from a particular direction (e.g., to the front of user 104) while potentially fully or partially canceling sound originating from other directions. In other words, a directional processing mode may selectively attenuate off-axis unwanted sounds. The directional processing mode may help user 104 understand conversations occurring in crowds or other noisy environments. In some examples, ear-wearable device(s) 102 may use beamforming or directional processing cues to implement or augment directional processing modes.

In some examples, ear-wearable device(s) 102 may reduce noise by canceling out or attenuating certain frequencies. Furthermore, in some examples, ear-wearable device(s) 102 may help user 104 enjoy audio media, such as music or sound components of visual media, by outputting sound based on audio data wirelessly transmitted to ear-wearable device(s) 102.

Ear-wearable device(s) 102 may be configured to communicate with each other. For instance, in any of the examples of this disclosure, ear-wearable device(s) 102 may communicate with each other using one or more wirelessly communication technologies. Example types of wireless communication technology include Near-Field Magnetic Induction (NFMI) technology, a 900 MHz technology, a Bluetooth® technology, a Wi-Fi® technology, audible sound signals, ultrasonic communication technology, infrared communication technology, an inductive communication technology, or another type of communication that does not rely on wires to transmit signals between devices. In some examples, ear-wearable device(s) 102 use a 2.4 GHz frequency band for wireless communication. In some examples of this disclosure, ear-wearable device(s) 102 may communicate with each other via non-wireless communication links, such as via one or more cables, direct electrical contacts, and so on.

In the example of FIG. 1, ear-wearable device 102A includes one or more processors 112A and a battery 114A. Ear-wearable device 102B includes one or more processors 112B and a battery 114B. This disclosure may refer to processors 112A and 112B collectively as "processors 112." Processors 112 may be implemented in circuitry and may include microprocessors, application-specific integrated circuits, digital signal processors, or other types of circuits. This disclosure may refer to battery 114A and battery 114B collectively as "batteries 114."

As noted above, ear-wearable devices 102A and 102B may be configured to communicate with one another. Accordingly, processors 112 may be configured to operate together as a processing system. Thus, discussion in this disclosure of actions performed by a processing system may be performed by one or more processors in one or more of ear-wearable device 102A or ear-wearable device 102B, either separately or in coordination. Moreover, it should be appreciated that, in some examples, the processing system does not include each of processors 112A or 112B. For instance, the processing system may be limited to processors 112A and not processors 112B; or the processing system may include processors 112B and not processors 112A. Components of ear-wearable device 102A, including processors 112A, may draw power for battery 114A. Components of ear-wearable device 102B, including processors 112B, may draw power for battery 114B. Batteries 114 may be rechargeable batteries, such as lithium-ion batteries, or other types of batteries.

Each of ear-wearable device(s) 102 may be configured to establish a respective communication link between ear-wearable device(s) 102 and one or more computing devices 108. For instance, computing devices 108 may comprise one or more mobile devices, server devices, personal computer devices, handheld devices, wireless access points, smart speaker devices, smart televisions, medical alarm devices, smart key fobs, smartwatches, smartphones, motion or presence sensor devices, smart displays, screen-enhanced smart speakers, wireless routers, wireless communication hubs, prosthetic devices, mobility devices, special-purpose devices, accessory devices, and/or other types of devices. Accessory devices may include devices that are configured specifically for use with ear-wearable devices 102. Example types of accessory devices may include charging cases for ear-wearable devices 102, storage cases for ear-wearable devices 102, media streamer devices, phone streamer devices, external microphone devices, remote controls for ear-wearable devices 102, and other types of devices specifically designed for use with ear-wearable devices 102. In some examples, one or more of computing devices 108 include devices used by third parties, such as healthcare professionals, family members, other ear-wearable device users, and other types of individuals. This disclosure may refer to a party other than user 104 as a third party. The communication links between ear-wearable devices 102 and one or more computing devices 108 may or may not occur concurrently with each other. Moreover, the communication links between ear-wearable devices 102 and one or more computing device(s) 108 may be established and disestablished multiple times.

In some examples, the communication link between a computing device 108 and ear-wearable device(s) 102 is a wireless communication link in which computing device 108 receives radio signals generated by ear-wearable device(s) 102. In some examples, the communication link between a computing device 108 and ear-wearable device(s) 102 is an optical communication channel in which computing device 108 receives light generated by the ear-wearable device. In some examples, the communication link between computing device 108 and ear-wearable device(s) 102 is an electrical communication channel in which computing device 108 receives electrical pulses generated by the ear-wearable device. In such examples, the communication channel does not involve any intermediate devices, such as network routers or gateways.

In some examples, the communication link between a computing device 108 and ear-wearable device(s) 102 may be established via a communication network, such as network 106. In some examples, ear-wearable device(s) 102 may communicate with computing device 108 via non-wireless communication links, such as via one or more cables, direct electrical contacts, and so on. Network 106 may include a variety of different types of communication networks. For example, network 106 may include one or more local area networks, wide area networks, the Internet, a cellular data network, or other types of networks. Network 106 may include wired and/or wireless communication links. In some examples, network 106 represents any public or private communications network, for transmitting data between computing systems and computing devices. Network 106 may include a cellular communication network, such as a 3G network, 4G LTE network, a 5G network, or other cellular communication network using another type of wireless communication technology. Network 106 may include a short-range communication network, such as Bluetooth®, Wi-Fi®, or other type of communication network including direct-connections, such as Wi-Fi® direct and inferred direct communication networks. Network 106 may include or be communicatively coupled to the Internet or other types of networks, both personal and private. Network 106 may include one or more network hubs, network switches, network routers, or any other network equipment, that are operatively inter-coupled thereby providing for the exchange of information between components of computing system 100. One or more of ear-wearable device(s) 102 and computing device(s) 108 may each be operatively coupled to network 106 using respective network links. The links coupling ear-wearable device(s) 102 and computing device(s) 108 to network 106 may be Ethernet or other types of network connections; such connections may be wireless and/or wired connections.

In a medical emergency event, a user, such as user 104, may be unable to communicate effectively with others. For example, user 104 may experience a stroke and may be unable to communicate to others any identifying information, medical conditions that may be important to determining treatment. As a result, ineffective communication may lead to increases in patient harm, length of hospital stay, and resource use. Improvements in technology allow for wearable devices to acquire this data from a user and transfer this data to an emergency response server. The emergency response server may then transfer this data to professional responders in the event of an emergency. However, professional responders may be far away from user 104 and may not be immediately available to provide assistance. Therefore, it is desirable to develop a system that is capable of broadcasting emergency events to notify nearby first-responders and providing treatment suggestions to relatively untrained first-responders.

In some examples, a health monitoring system may be implemented on ear-wearable device(s) 102. The health monitoring system may determine user 104 of ear-wearable device(s) 102 is experiencing a potential medical event based on both the health data of user 104 and a captured user response. In response to determining that user 104 of ear-wearable device 102 is experiencing a potential medical event, the health monitoring system may cause ear-wearable devices 102 to send a wireless communication request to a plurality of nearby companion devices, such as computing device(s) 108. In response to the wireless communication request being accepted by a companion device of the plurality of companion devices (e.g., computing device 108A), the health monitoring system may cause ear-wearable device(s) 102 to send user data via a communication link between the companion device (e.g., computing device 108A) and ear-wearable device(s) 102. The user data includes information related to the potential medical event, such as device location, user health information, and treatment suggestions, etc. In some examples, the user data may include different information depending on the type of the potential medical event. In this way, a device or person reviewing the information related to the potential medical event may obtain relevant information specific to the type of potential medical event.

In some examples, the health monitoring system may make a first preliminary determination that user 104 of ear-wearable device(s) 102 is experiencing a potential medical event based on health data of user 104. Examples of potential medical events may include anomalous heart rhythms, low blood pressure, hypo- or hyper-glycemia, falls, seizures, and so on. Health data may include data determined based on first signals captured from first sensors of ear-wearable device(s) 102. For instance, ear-wearable device(s) 102 may include one or more IMU sensors and may use IMU signals to determine whether user 104 is experiencing a potential medical event (e.g., a fall incident). As another example, ear-wearable device(s) 102 may include one or more PPG sensors and may use PPG signals to determine whether user 104 is experiencing a potential medical event (e.g., a fall incident). In some examples, ear-wearable device(s) 102 may make a first preliminary determination that user 104 of ear-wearable device(s) 102 is experiencing a potential medical event based on a combination of health signals. For example, ear-wearable device(s) 102 may detect a rapid drop in the blood sugar level of user 104, a severe slowdown of the heart rate of user 104, and a possible fall, and may determine user 104 is experiencing a potential medical event (e.g., a diabetic incident, a heart issue, or a breathing issue) based on the combination of health data.

In some examples, the health monitoring system may make a second preliminary determination that user 104 of ear-wearable device(s) 104 is experiencing a potential medical event based on a user response captured by ear-wearable device(s) 102. For instance, in response to the first preliminary determination being that user 104 of ear-wearable device(s) 102 is experiencing a potential medical event, wearable device(s) 102 may provide an audible message to user 104 via ear-wearable device (s) 102. For example, the health monitoring system may cause ear-wearable device(s) 102 to output a "Do you need help?" audible message to user 104, and ear-wearable device(s) 102 may capture a user response from user 104. In some examples, ear-wearable device(s) 102 may capture a voice response from user 104 via one or more microphones. In some examples, ear-wearable device(s) 102 may capture an action response from user 104 via one or more motion sensors.

In some examples, the health monitoring system may determine, based on both the first preliminary determination and the second preliminary determination, whether user 104 of ear-wearable device(s) 102 is experiencing a potential medical event. Using both the signals detected from one or more sensors of the ear-wearable device(s) 102 and captured user responses to determine whether user 104 of ear-wearable device(s) 102 is experiencing a potential medical event may be more robust than using only the signals detected from one or more sensors of the ear-wearable device(s) 102 to determine whether user 104 is experiencing a potential medical event. That is, use of both the signals detected from one or more sensors of the ear-wearable device(s) 102 and captured user responses to determine whether user 104 of ear-wearable device(s) 102 is experiencing a potential medical event may reduce over- and under-reporting of medical emergency events. This is because the health monitoring system may be able to use captured user responses as a check on emergency event detections based on the signals detected from one or more sensors of the ear-wearable device(s) 102.

In response to determining that user 104 of ear-wearable device(s) 102 is experiencing a potential medical event, the health monitoring system may cause ear-wearable device(s) 102 to send a wireless communication request to a plurality of nearby companion devices, such as computing devices 108A-108N. The wireless communication request may include information to inform users of the nearby companion devices that a medical emergency event is happening nearby. In some examples, the wireless communication request may be sent via a wireless transport, such as a personal area network (PAN) transport, which may include Bluetooth® communication, low energy and high (or, in other words, normal or Bluetooth® classic) energy versions, a wireless local area network (WLAN) connection, and the like.

In some examples, the wireless communication request may be transmitted from ear-wearable device(s) 102 to the plurality of nearby companion devices 108 via Bluetooth® communication in multiple modes. For example, ear-wearable device(s) 102 may initiate the wireless communication request in a normal mode, which transmits the wireless communication request in a normal data rate (e.g., 1 Mbit/s). If the wireless communication request transmitted in the normal mode has not been accepted by a companion device, ear-wearable device(s) 102 may re-initiate the wireless communication request in an extended range mode, which transmits the wireless communication request in a reduced data rate (e.g., 500 Kbit/s) compared to the normal data rate of the normal mode. Because of the reduced data rate, the extended range mode extends the communication range compared to the normal mode. If the wireless communication request transmitted in the extended mode has not been accepted by a companion device, ear-wearable device(s) 102 may re-send the wireless communication request in a long range mode, which transmit the wireless communication request in a lower data rate (e.g., 125 Kbit/s) compare to the reduced data rate of the extended range mode. The long range mode further extends communication range compare to the extended range mode.

In some examples, ear-wearable device(s) 102 may use nearby Bluetooth® capable devices to further transmit the wireless communication request. For example, ear-wearable device(s) 102 may be limited in wireless output power, which may severely limit the range that the signal would reach. By using nearby Bluetooth® capable devices to transmit the communication request, ear-wearable device(s) 102 may boost the communication range. Examples of Bluetooth® capable devices may include Bluetooth® speakers, hearing aid accessories, a tablet, or an automated external defibrillator (AED) that has Bluetooth® connectivity. In some examples, a Bluetooth® capable device may be connected to an emergency services line, which may automatically call 911 or send a similar alert to a nearby group of individuals. For example, a Bluetooth® capable device may be configured to send a text message to office workers trained in first aid. The Bluetooth® capable device's location could also be detected and sent out by Bluetooth® signal to people nearby.

In response to the wireless communication request being accepted by a companion device of the plurality of companion devices (e.g., computing device 108A), the health monitoring system may cause ear-wearable device(s) 102 to send user data via a communication link between the companion device (e.g., computing device 108A) and ear-wearable device(s) 102. In some examples, the user data includes information related to the medical emergency event, such as device location data, emergency event data, and treatment suggestion data, etc. In some examples, the information related to the medical emergency event may be dependent on a type of the medical emergency event. For example, the user data sent by ear-wearable device(s) may include different information based on whether user 104 is likely experiencing a heart attack, a stroke, a diabetic episode, or another type of medical emergency event.

In some examples, device location data may include global positioning system (GPS) data, and the companion device (e.g., computing device 108A) may utilize the received GPS data to determine the current location of ear-wearable device(s) 102. In some examples, device location data may include received signal strength indication (RSSI) data and/or Time of Flight (ToF) data, and the companion device (e.g., computing device 108A) may utilize RSSI data and/or ToF data to determine the current distance between the companion device and ear-wearable device(s) 102. The companion device may further determine the direction of ear-wearable device(s) 102 relative to the companion device. Use RSSI data and/or ToF data may help to improve the accuracy of the determined location of ear-wearable device(s) 102.

In some examples, emergency event data may include various types of data that relate to the physical health information of user 104. For instance, user health information data includes information generated based on second signals generated by one or more second sensors that are included in ear-wearable device(s) 102. In some examples, ear-wearable device(s) 102 may include one or more of electroencephalography (EEG) sensors and/or electrocardiogram (ECG) sensors. Ear-wearable device(s) 102 may transmit EEG data and/or ECG data to the companion device, and the companion device may process the received EEG data and/or ECG data and display an EEG and/or ECG waveform. In some examples, ear-wearable device(s) 102 may process the EEG data and/or ECG data to determine various types of data that relate to the physical health information of user 104, including heart rate, respiration rate, blood glucose level, oxygen saturation of user 104, and other data related to user 104. Ear-wearable device(s) 102 may further transmit the various types of data that relate to the physical health information of user 104 to the companion device (e.g., computing device 108A).

In some examples, treatment suggestion data may include instructions on how to apply immediate treatment to user 104 of ear-wearable device(s) 102. The treatment suggestion data may enable relatively untrained first-responders to provide proper pre-hospital care to user 104 of ear-wearable device(s) 102.

In some examples, the user data transmitted from ear-wearable device(s) 102 to the companion device (e.g., computing device 108A) may include data instructing the companion device to generate an audible alert to notify the user of the companion device to listen to ear-wearable device(s) 102. Ear-wearable device(s) 102 may output an audible message to the user of the companion device, providing user identity information, relevant medical history, current prescription records, emergency contact information of user 104 of ear-wearable device(s) 102, and other data related to user 104. In some examples, ear-wearable device(s) 102 may further output audible instructions on how to apply immediate treatment to user 104 of ear-wearable device(s) 102. In this example, the audible instructions may help the user of the companion device (e.g., computing device 108A) to efficiently provide proper pre-hospital care to user 104 of ear-wearable device(s) 102. In some examples, the audible message may be transmitted from ear-wearable device(s) 102 to a trusted companion device (e.g., computing device 108N). For example, medical personnel carrying a trusted companion device may request the user data from ear-wearable device(s) 102. Ear-wearable device(s) 102 may authenticate the trusted companion device using a digital certificate, and may transfer the user data upon authentication. In accordance with the techniques of this disclosure, ear-wearable device(s) 102 only transfer user data to an external device with explicit permissions from user 104. Absent the user's explicit authorization, ear-wearable device(s) 102 will not transfer user data to an external device.

Figure 2:
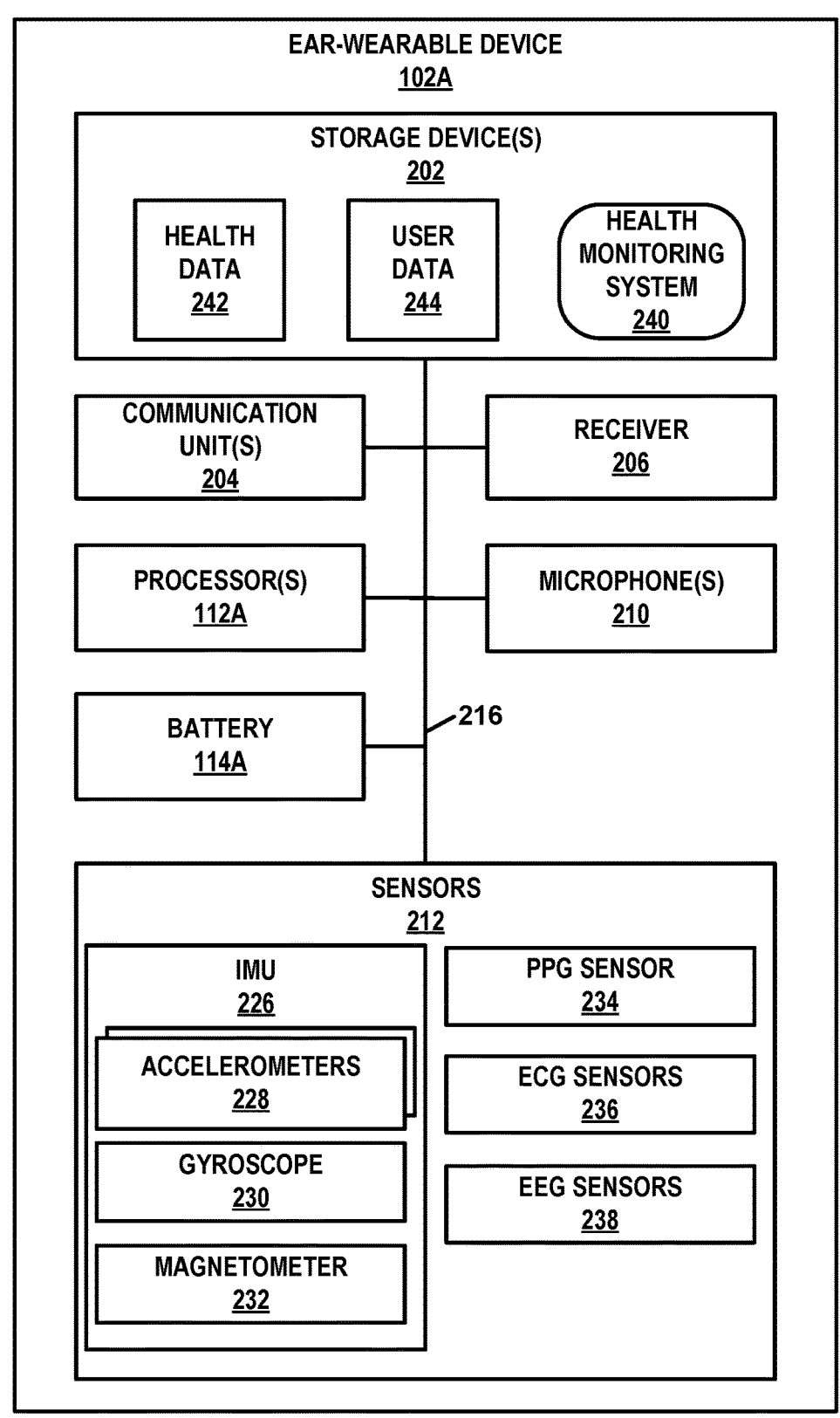
FIG. 2 is a block diagram illustrating example components of an ear-wearable device, in accordance with one or more aspects of this disclosure.

FIG. 2 is a block diagram illustrating example components of ear-wearable device 102A, in accordance with one or more aspects of this disclosure. Ear-wearable device 102B may include the same or similar components of ear-wearable device 102A shown in the example of FIG. 2. Thus, discussion of ear-wearable device 102A may apply with respect to ear-wearable device 102B.

In the example of FIG. 2, ear-wearable device 102A comprises one or more storage devices 202, one or more communication units 204, a receiver 206, one or more processors 112A, one or more microphones 210, a set of sensors 212, a battery 114A, and one or more communication channels 216. Communication channels 216 provide communication between storage devices 202, communication unit(s) 204, receiver 206, processor(s) 112A, a microphone(s) 210, and sensors 212. Components 202, 204, 206, 112A, 210, and 212 may draw electrical power from battery 114A.

Battery 114A may include any suitable arrangement of disposable batteries, along or in combination with rechargeable batteries, to provide electric power to storage devices 202, communication units 204, receiver 206, processors 112A, microphones 210, and sensors 212.

In the example of FIG. 2, each of components 202, 204, 206, 112A, 210, 212, 114A, and 216 are contained within a single housing. However, in other examples of this disclosure, components 202, 204, 206, 112A, 210, 212, 114A, and 216 may be distributed among two or more housings. For instance, in an example where ear-wearable device 102A is a RIC device, receiver 206 and one or more of sensors 212 may be included in an in-ear housing separate from a behind-the-ear housing that contains the remaining components of ear-wearable device 102A. In such examples, a RIC cable may connect the two housings.

Furthermore, in the example of FIG. 2, sensors 212 include an inertial measurement unit (IMU) 226 that is configured to generate data regarding the motion of ear-wearable device 102A. IMU 226 may include a set of sensors. For instance, in the example of FIG. 2, IMU 226 includes one or more of accelerometers 228, a gyroscope 230, a magnetometer 232, combinations thereof, and/or other sensors for determining the motion of ear-wearable device 102A. Furthermore, in the example of FIG. 2, ear-wearable device 102A may include a photoplethysmography (PPG) sensor 234, one or more electrocardiogram (ECG) sensors 236, and one or more electroencephalography (EEG) sensors 238. Ear-wearable device 102A may further include one or more of blood oximetry sensors, blood pressure sensors, electrocardiograph (EKG) sensors, body temperature sensors, environmental temperature sensors, environmental pressure sensors, environmental humidity sensors, skin galvanic response sensors, and/or other types of sensors. In other examples, ear-wearable device 102A and sensors 212 may include more, fewer, or different components.

Storage devices 202 may store data. Storage devices 202 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage devices 202 may further be configured for long-term storage of information as non-volatile memory space and may retain information after power on/off cycles. Examples of non-volatile memory configurations may include flash memories, or forms of electrically programmable memories (EPROM) or electrically erasable and programmable (EEPROM) memories.

Communication unit(s) 204 may enable ear-wearable device 102A to send data to and receive data from one or more other devices, such as another ear-wearable device, an accessory device, a mobile device, or other types of device. Communication unit(s) 204 may enable ear-wearable device 102A using wireless or non-wireless communication technologies. For instance, communication unit(s) 204 may enable ear-wearable device 102A to communicate using one or more of various types of wireless technology, such as a Bluetooth® technology, 3G, 4G, 4G LTE, 5G, ZigBee, Wi-Fi®, Near-Field Magnetic Induction (NFMI), ultrasonic communication, infrared (IR) communication, or another wireless communication technology. In some examples, communication unit(s) 204 may enable ear-wearable device 102A to communicate using a cable-based technology, such as a Universal Serial Bus (USB) technology.

Receiver 206 comprises one or more speakers for generating audible sound. Microphone(s) 210 detects incoming sound and generates audio data (e.g., an analog or digital electrical signal) representing the incoming sound. In accordance with the techniques of this disclosure, a health monitoring system 240 will only capture audio using receiver 206 and/or microphone 210 with explicit permissions from user 104. Absent the user's explicit authorization, health monitoring system 240 will not capture spoken audio data from microphone(s) 210.

Processor(s) 112A may be processing circuits configured to perform various activities. For example, processor(s) 112A may process the signal generated by microphone(s) 210 to enhance, amplify, or cancel-out particular channels within the incoming sound. Processor(s) 112A may then cause receiver 206 to generate sound based on the processed signal. In some examples, processor(s) 112A include one or more digital signal processors (DSPs). In some examples, processor(s) 112A may cause communication unit(s) 204 to transmit one or more of various types of data. For example, processor(s) 112A may cause communication unit(s) 204 to transmit data to computing device(s) 108. Furthermore, communication unit(s) 204 may receive audio data from computing device(s) 108, and processor(s) 112A may cause receiver 206 to output sound based on the audio data.

In the example of FIG. 2, storage device(s) 202 may store health data 242, user data 244, and health monitoring system 240. Health monitoring system 240 may generate health data 242 and user data 244. Health data 242 includes data determined based on signals captured from various sensors of ear-wearable device(s) 102, such as EEG data, ECG data, blood oximetry values, blood pressures, EKG data, body temperatures, skin galvanic response data, etc. User data 244 includes information related to the potential medical event, such as device location, emergency event data, and treatment suggestions, etc.

In some examples, health monitoring system 240 may make a first preliminary determination that user 104 of ear-wearable device 102A is experiencing a potential medical event based on health data 242 (and thus based on signals generated by signals captured by one or more sensors of ear-wearable device(s) 102). For example, health monitoring system 240 may generate a health score indicating health condition of user 104 of ear-wearable device(s) 102 based on health data 242. In accordance with the techniques of this disclosure, health monitoring system 240 may assign a numerical value that represents the relative health of user 104. The numerical value is described herein as a "health score" and can be used to access to the health of user 104 based on health data 242 collected from user 104. The health score is calculated based on health data 242 using an algorithm. In some examples, the algorithm may use predetermined weighting factors to assign a relative value of each of parameters that are used to calculate the health score and the algorithm calculates the health score by combining the weighted parameters in accordance with the algorithm. Health monitoring system 240 may compare the determined health score with a health threshold and determine that user 104 of ear-wearable device(s) 102 is experiencing a potential medical event based on the health score fails to satisfy the health threshold. In some examples, an alert may alert user 104 of ear-wearable device(s) 102 or another person to the occurrence of a medical emergency. In other words, health monitoring system 240 may generate, based on the health score, an alert to user 104 of hearing-assistance device(s) 102 or another person. Ear-wearable device(s) 102 may transmit an alert to a caregiver, healthcare professional, family member, or other person or persons. For instance, health monitoring system 240 may generate an alert if health monitoring system 240 determines that the health score below the health threshold for a threshold amount of time (e.g., a few minutes). In some examples, responsive to declaration of an alert, an audible message may be provided to user 104 of ear-wearable device(s) 102.

In some examples, health monitoring system 240 may make a second preliminary determination that user 104 of ear-wearable device 102A is experiencing a potential medical event based on a user response captured by ear-wearable device 102A. For instance, health monitoring system 240 may cause ear-wearable device 102A to output an audible message based on the first preliminary determination being that user 104 of ear-wearable device(s) 102 is experiencing a potential medical event. Health monitoring system 240 may then make a second preliminary determination that user 104 of ear-wearable device(s) 102 is experiencing a potential medical event based on an action response (e.g., a nod) detected by IMU 226 or a voice response detected by microphone(s) 210. In some examples, a user may be unconscious (e.g., being knocked unconscious during a fall, paralysis from a stroke, loss of consciousness from a sudden cardiac event, etc.) and may not be able to respond to the audible message. In such examples, health monitoring system 240 may make a second preliminary determination that user 104 of ear-wearable device(s) 102 is experiencing a potential medical event based on a non-response to the audible message for a pre-defined time period. Health monitoring system 240 may further determine, based on both the first preliminary determination and the second preliminary determination, whether user 104 of ear-wearable device 102A is experiencing a potential medical event.

In response to determining that user 104 of ear-wearable device 102A is experiencing a potential medical event, health monitoring system 240 may cause communication unit(s) 204 to send a wireless communication request to a plurality of companion devices (e.g., computing device(s) 108). In some examples, the wireless communication request is a Bluetooth® pairing request. The Bluetooth® pairing request may include a notification of the potential emergency event. In response to the wireless communication request being accepted by a companion device of the plurality of companion devices (e.g., computing device 108A), health monitoring system 240 may cause ear-wearable device(s) to send health data 242 and/or user data 246 via a communication link between the companion device and ear-wearable device 102A. In some examples, the wireless communication link is a Bluetooth® communication link.

In some examples, a Wi-Fi® access point may be pinged by either the ear-wearable device 102 or by a mobile device (e.g., computing device 108A) for user 104. Using a Wi-Fi® access point, health monitoring system 240 may cause ear-wearable device(s) to send health data 242 and/or user data 246 between the companion device and ear-wearable device 102A securely. In some examples, health monitoring system 240 may cause ear-wearable device(s) to push health data 242 and/or user data 246 to an app downloaded on computing device(s) 108 (e.g., an app downloaded by on- or off-duty EMTs, police or security officers, and firefighters, as well as any member of the public who is trained in first aid and wants to be available in case of an emergency). Computing device(s) 108 may then retrieve health data 242 and/or user data 246 through the app.

Figure 3:
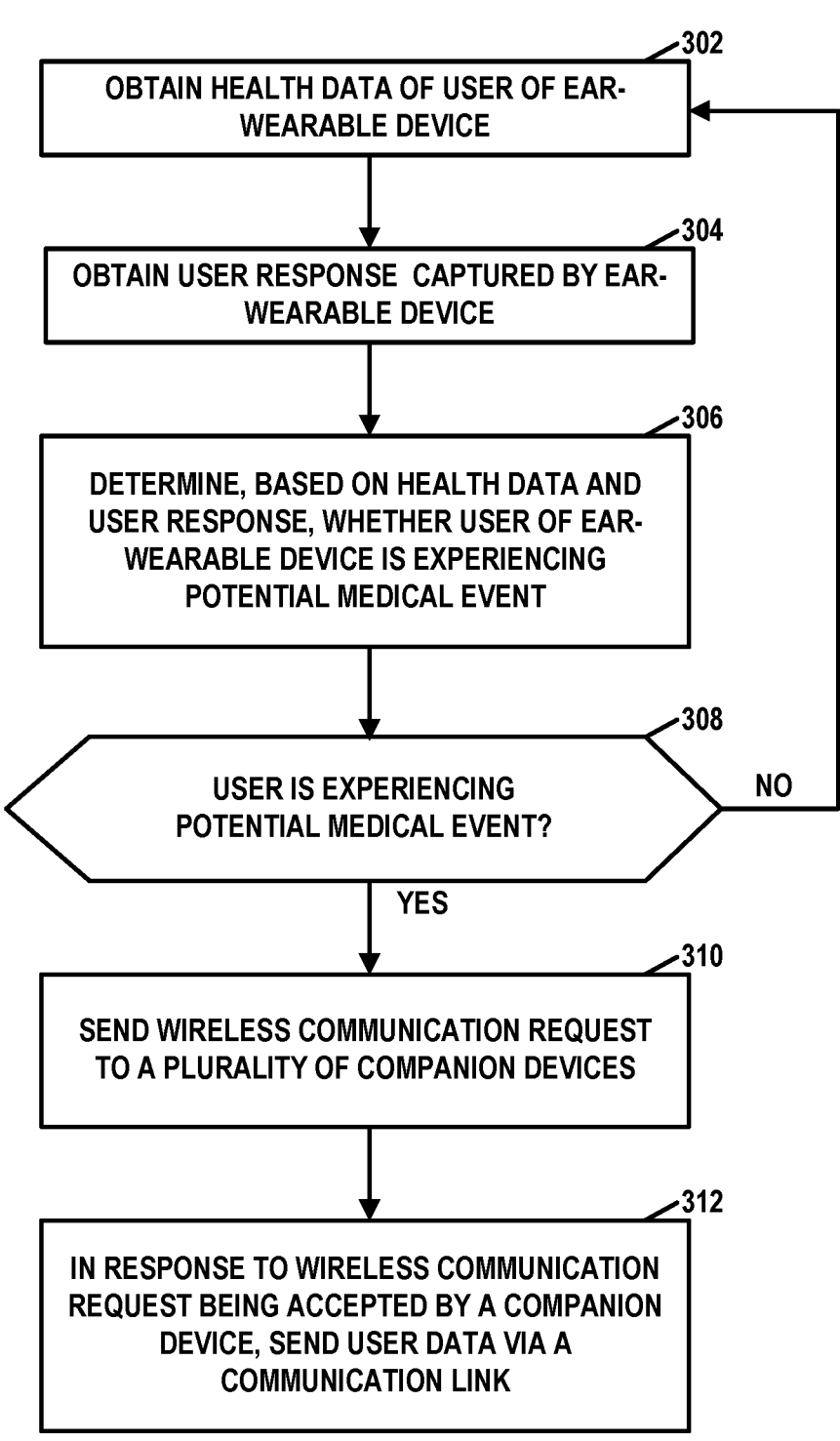
FIG. 3 is a flowchart illustrating a first example operation of ear-wearable device(s) in accordance with a technique of this disclosure.

FIG. 3 is a flowchart illustrating a first example operation of ear-wearable device(s) 102 in accordance with a technique of this disclosure. The flowcharts of this disclosure are provided as examples. In other examples, operations shown in the flowcharts may include more, fewer, or different actions, or actions may be performed in different orders or in parallel.

In the example of FIG. 3, a health monitoring system, such as health monitoring system 240 (FIG. 2), may obtain health data of user 104 of ear-wearable device(s) 102 (302). In some examples, the health data includes data determined based on first signals captured from first sensors of ear-wearable device(s) 102, such as EEG data, ECG data, blood oximetry values, blood pressures, EKG data, body temperatures, skin galvanic response data, etc. Health monitoring system 240 may further obtain a user response captured by ear-wearable device(s) 102 (304). In some examples, the captured user response may include a voice response captured by microphone(s) 210 (FIG. 2) and/or an action response captured by IMU 226 (FIG. 2). In some examples, the captured user response may include a non-response to an audible message for a pre-defined time period.

Furthermore, in the example of FIG. 3, health monitoring system 240 may determine, based on the health data and the user response, whether a user of ear-wearable device(s) 102 is experiencing a potential medical event (306). Health monitoring system 240 may make this determination in any of various ways, including those described elsewhere in this disclosure.

In response to determining user 104 is not experiencing a potential medical event ("NO" branch of 308), health monitoring system 240 may continue to obtain health data of user 104 of ear-wearable device(s) 102 (302). However, if health monitoring system 240 determines that user 104 is experiencing a potential medical event ("YES" branch of 308), health monitoring system 240 may cause ear-wearable device 102 to send a wireless communication request to a plurality of companion devices, such as computing devices 108A-108N (FIG. 1) (310). In response to the wireless communication request being accepted by a companion device of the plurality of companion devices, health monitoring system 240 may cause ear-wearable device(s) 102 to send user data 246 (FIG. 2) via a communication link between the companion device and ear-wearable device(s) 102 (312). In some examples, the user data includes information generated based on second signals generated by one or more second sensors that are included in ear-wearable device(s) 102. For examples, the user data may include information related to the potential medical event, such as device location, user health information, and treatment suggestions, etc. In some examples, health monitoring system 240 may cause ear-wearable device(s) 102 to send an audio notification related to the user's health (e.g., audio data containing user data 246) via the communication link between the companion device and ear-wearable device(s) 102.

Figure 4:
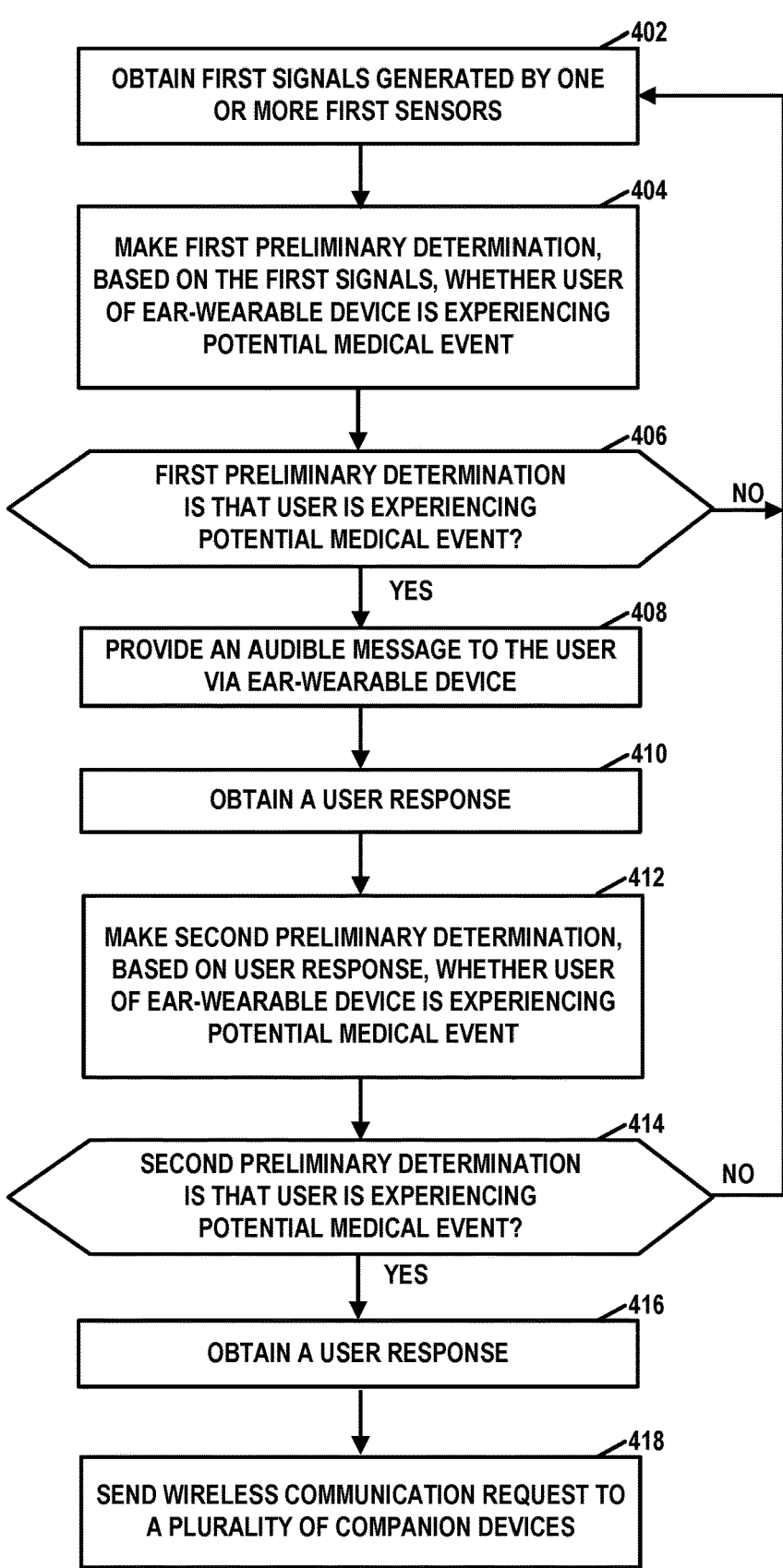
FIG. 4 is a flowchart illustrating a second example operation of ear-wearable device(s) in accordance with a technique of this disclosure.

FIG. 4 is a flowchart illustrating a second example operation of ear-wearable device(s) in accordance with a technique of this disclosure. In the example of FIG. 4, health monitoring system 240 may obtain first signals generated by one or more first sensors (402). Additionally, in the example of FIG. 4, health monitoring system 240 may make a first preliminary determination that user 104 is experiencing a potential medical event based on the first signals (404). For instance, health monitoring system 240 may make the first preliminary determination in the manner described in examples provided elsewhere in this disclosure for determining whether user 104 is experiencing a potential medical event based on the first signals. If the first preliminary determination is that user 104 is not experiencing a potential medical event ("NO" branch of 406), health monitoring system 240 may repeat actions (402) and (404).

If the first preliminary determination is that user 104 is experiencing a potential medical event ("YES" branch of 406), health monitoring system 240 may provide an audible message to user 104 via ear-wearable device(s) 102 (408). Health monitoring system 240 may further obtain a user response (e.g., a voice response, an action response, or a non-response to the audible message for a pre-defined time period) via ear-wearable device(s) 102 (410). Additionally, health monitoring system 240 may make a second preliminary determination that user 104 is experiencing a potential medical event based on the user response (412).

If the second preliminary determination is that user 104 is not experiencing a potential medical event ("NO" branch of 414), health monitoring system 240 may repeat actions (402) through (412), as needed. However, if the second preliminary determination is that user 104 is experiencing a potential medical event ("YES" branch of 414), health monitoring system 240 may determine that user 104 is experiencing a potential medical event based on both the first preliminary determination and the second preliminary determination being that 104 user 104 is experiencing a potential medical event. Accordingly, health monitoring system 240 may then cause ear-wearable device(s) 102 to send a wireless communication request to a plurality of companion devices (418). Health monitoring system 240 may cause ear-wearable device(s) 102 to send a wireless communication request to a plurality of companion devices in accordance with any of the examples provided elsewhere in this disclosure.

In some examples, an ear-wearable system may be implemented on ear-wearable device(s) 102, allowing user 104 to track the location of ear-wearable device(s) 102. For instance, user 104 may lose one of ear-wearable device(s) 102 (e.g., ear-wearable device 102A) and may not notice this for some time. When user 104 loses ear-wearable device 102A in a public place, it may be very difficult for them to locate it again. Thus, it would be advantageous to be able to continuously and automatically have access to location information about ear-wearable device 102A. In some examples, a remaining ear-wearable device 102B may send an audio alert to user 104 when ear-wearable device 102A loses connection with ear-wearable device 102B for a pre-defined period of time, informing user 104 that ear-wearable device 102A is missing. Ear-wearable device 102B may also inform user 104 how long it has been since the last connection with ear-wearable device 102B was made and/or the location of user 104 when ear-wearable device 102B was last connected to a trusted device (e.g., computing device(s) 108). In some examples, ear-wearable device 102B may be configured to output an audio message to instruct a passerby to return ear-wearable device 102B to user 104. When ear-wearable device 102A loses connection with ear-wearable device 102B for a predefined period of time, ear-wearable device 102A is not able to transmit out a medical event emergency, which prevents ear-wearable device 102A from triging false alerts (e.g., generating false alerts based on inaccurately tracked heart rate or oxygen saturation during the event of losing wearable device 102B).

In some examples, the ear-wearable system may be implemented on ear-wearable device(s) 102, allowing user 104 to control ear-wearable device(s) 102 via audible cues. In some examples, ear-wearable device(s) 102 may include a 32 kilohertz (kHz) oscillator, which can act as a real time clock when ear-wearable device 102A loses connection with a trusted device (e.g., computing device(s) 108). The ear-wearable system may enable ear-wearable device(s) 102 to state the real-time when prompted by user 104, or act as an alarm or stopwatch (i.e., ring in 20 minutes or ring at 3:30 PM). In some examples, the ear-wearable system may be used to determine how long user 104 has been walking or watching TV. In some examples, ear-wearable device(s) 102 may be connected to a mobile device of user 104 (e.g., computing device(s) 108), and the ear-wearable system may cause ear-wearable device(s) 102 to interface with the mobile device to access a calendar of user 104.

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
   obtaining, by a processing system, one or more first signals that are generated by one or more first sensors that are included in an ear-wearable device;
   making a first preliminary determination, by the processing system, that a user of the ear-wearable device is experiencing a potential medical event based on the one or more first signals;
   in response to the first preliminary determination that the user of the ear-wearable device is experiencing the potential medical event, requesting, by the processing system, a user response;
   making a second preliminary determination, by the processing system, that the user of the ear-wearable device is experiencing the potential medical event based on the user response captured by the ear-wearable device;
   determining, by the processing system, that the user of the ear-wearable device is experiencing the potential medical event based on both the first preliminary determination and the second preliminary determination;
   in response to determining that the user of the ear-wearable device is experiencing the potential medical event, sending, from the ear-wearable device to a plurality of companion devices, a wireless communication request; and
   in response to the wireless communication request being accepted by a companion device of the plurality of companion devices, sending user data via a communication link between the companion device and the ear-wearable device, wherein the user data comprises information generated based on one or more second signals generated by one or more second sensors that are included in the ear-wearable device.

2. The method of claim 1, further comprises:
   in response to the first preliminary determination being that the user of the ear-wearable device is experiencing the potential medical event, providing an audible message to the user via the ear-wearable device.

3. The method of claim 2, wherein the user response captured by the ear-wearable device comprises a non-response to the audible message for a pre-defined time period.

4. The method of claim 1, wherein the user response captured by the ear-wearable device comprises at least a voice response or an action response.

5. The method of claim 1, wherein the user data further comprises one or more of a location of the ear-wearable device, user profile information of the user of the ear-wearable device, or emergency contact information of the user of the ear-wearable device.

6. The method of claim 1, wherein the user data further comprises one or more of heart rate, respiration rate, blood glucose level, or oxygen saturation.

7. The method of claim 1, wherein the one or more first signals comprise one or more of inertial measurement unit (IMU) signals and photoplethysmography (PPG) signals.

8. The method of claim 1, wherein the one or more second signals comprise one or more of electroencephalography (EEG) signals and electrocardiogram (ECG) signals.

9. The method of claim 1, wherein the wireless communication request comprises a BLUETOOTH pairing request, and wherein the communication link comprises a BLUETOOTH communication link.

10. The method of claim 1, wherein making the first preliminary determination that the user of the ear-wearable device is experiencing the potential medical event based on the one or more first signals comprises:

generating a health score based on the one or more first signals;

comparing the health score with a health threshold; and determining that the user of the ear-wearable device is experiencing the potential medical event based on the health score failing to satisfy the health threshold.

11. The method of claim 1, further comprising:

sending an audio notification related to the user's health via the communication link between the companion device and the ear-wearable device.

12. A computing system comprising:

a data storage system configured to store user data related to a user of an ear-wearable device; and one or more processors implemented in circuitry, the one or more processors configured to:

obtain one or more first signals that are generated by one or more first sensors that are included in the ear-wearable device;

make a first preliminary determination that the user of the ear-wearable device is experiencing a potential medical event based on the one or more first signals;

in response to the first preliminary determination that the user of the ear-wearable device is experiencing the potential medical event, request a user response;

make a second preliminary determination that the user of the ear-wearable device is experiencing the potential medical event based on the user response captured by the ear-wearable device;

determine that the user of the ear-wearable device is experiencing the potential medical event based on both the first preliminary determination and the second preliminary determination;

in response to determining that the user of the ear-wearable device is experiencing the potential medical event, send, from the ear-wearable device to a plurality of companion devices, a wireless communication request; and in response to the wireless communication request being accepted by a companion device of the plurality of companion devices, send the user data via a communication link between the companion device and the ear-wearable device, wherein the user data comprises information generated based on one or more second signals generated by one or more second sensors that are included in the ear-wearable device.

13. The computing system of claim 12, wherein the one or more processors are configured to:

in response to the first preliminary determination being that the user of the ear-wearable device is experiencing the potential medical event, provide an audible message to the user via the ear-wearable device.

14. The computing system of claim 12, wherein the user response captured by the ear-wearable device comprises at least a voice response or an action response.

15. The computing system of claim 12, wherein the user data further comprises one or more of a location of the ear-wearable device, user profile information of the user of the ear-wearable device, or emergency contact information of the user of the ear-wearable device.

16. The computing system of claim 12, wherein the user data further comprises one or more of heart rate, respiration rate, blood glucose level, or oxygen saturation.

17. The computing system of claim 12, wherein the one or more first signals comprise one or more of IMU signals and PPG signals.

18. The computing system of claim 12, wherein the one or more second signals comprise one or more of EEG signals and ECG signals.

19. The computing system of claim 12, wherein the one or more processors are configured to:

send an audio notification related to the user's health via the communication link between the companion device and the ear-wearable device.

20. An ear-wearable device comprising:

one or more first sensors;

one or more second sensors; and one or more processors implemented in circuitry, the one or more processors configured to:

obtain one or more first signals that are generated by the one or more first sensors;

make a first preliminary determination that a user of the ear-wearable device is experiencing a potential medical event based on the one or more first signals;

in response to the first preliminary determination that the user of the ear-wearable device is experiencing the potential medical event, request a user response;

make a second preliminary determination that the user of the ear-wearable device is experiencing the potential medical event based on the user response captured by the ear-wearable device;

determine that the user of the ear-wearable device is experiencing the potential medical event based on both the first preliminary determination and the second preliminary determination;

in response to determining that the user of the ear-wearable device is experiencing the potential medical event, send, from the ear-wearable device to a plurality of companion devices, a wireless communication request; and in response to the wireless communication request being accepted by a companion device of the plurality of companion devices, send user data via a communication link between the companion device and the ear-wearable device, wherein the user data comprises information generated based on one or more second signals generated by the one or more second sensors.

21. A non-transitory computer-readable data storage medium having instructions stored thereon that, when executed, cause one or more processing circuits to:

obtain one or more first signals that are generated by one or more first sensors that are included in an ear-wearable device;

make a first preliminary determination that a user of the ear-wearable device is experiencing a potential medical event based on the one or more first signals;

in response to the first preliminary determination that the user of the ear-wearable device is experiencing the potential medical event, request a user response;

make a second preliminary determination that the user of the ear-wearable device is experiencing the potential medical event based on the user response captured by the ear-wearable device;

determine that the user of the ear-wearable device is experiencing the potential medical event based on both the first preliminary determination and the second preliminary determination;

in response to determining that the user of the ear-wearable device is experiencing the potential medical event, send, from the ear-wearable device to a plurality of companion devices, a wireless communication request; and in response to the wireless communication request being accepted by a companion device of the plurality of companion devices, send user data via a communication link between the companion device and the ear-wearable device, wherein the user data comprises information generated based on one or more second signals generated by one or more second sensors that are included in the ear-wearable device.

* * * * *